United States Patent [19]

Tejima et al.

[11] Patent Number: 4,584,190

[45] Date of Patent: Apr. 22, 1986

[54] NOVEL CHALCONE DERIVATIVES AND ULTRAVIOLET ABSORBERS COMPRISING THE SAME

[75] Inventors: Tohru Tejima, Tochigi; Koichi Nakamura, Ichikaimachi; Michihiro Hattori, Utsunomiya; Shinichi Masuda, Wakayama; Genji Imokawa; Naotake Takaishi, both of Utsunomiya, all of Japan

[73] Assignee: Kao Corporation, Tokyo, Japan

[21] Appl. No.: 669,888

[22] Filed: Nov. 9, 1984

[30] Foreign Application Priority Data

Nov. 17, 1983 [JP] Japan ................... 58-216913

[51] Int. Cl.$^4$ .................. A61K 7/42; C07C 69/017
[52] U.S. Cl. .................... 424/59; 260/410.5; 560/138
[58] Field of Search ............ 260/410.5; 560/138; 424/59; 568/334

[56] References Cited

U.S. PATENT DOCUMENTS 3,479,428 11/1969 Bryce et al. ............... 424/59
3,751,563 8/1973 Richardson et al. ........ 424/59
4,279,930 7/1981 Hall et al. ................ 568/334

FOREIGN PATENT DOCUMENTS 69672 12/1967 German Democratic Rep. ... 424/59

OTHER PUBLICATIONS

Namariyama et al., Chem. Abstracts 91:166351u (1979), "Photosensitivity of Styryl Ketone Polymers".

Primary Examiner—Bernard Helfin
Attorney, Agent, or Firm—Oblon, Fisher, Spivak, McClelland & Maier

[57] ABSTRACT

A chalcone derivative of the formula (I):

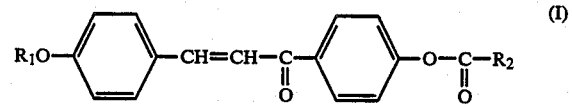

in which $R_1$ represents hydrogen or a methyl group, and $R_2$ represents a linear or branched aliphatic hydrocarbon group having from 2 to 24 carbon atoms.

The derivative is effective in protecting the skin when made into ultraviolet absorbing agents including an anti-sunburn oil, since it has the maximum absorbing capacity at a wave length in the vicinity of 350 nm, does not irritate the skin and is highly compatible with a cosmetic base.

6 Claims, 1 Drawing Figure

NOVEL CHALCONE DERIVATIVES AND ULTRAVIOLET ABSORBERS COMPRISING THE SAME

BACKGROUND OF THE INVENTION (i) Field of the Invention:

This invention relates to novel chalcone derivatives and ultraviolet absorbers comprising the derivatives.

(ii) Description of the Prior Art:

It is known that ultraviolet rays bring about various changes in the skin. From the dermatological standpoint, the ultraviolet rays are broadly classified on the basis of the wavelength into a long wavelength ultraviolet ray of 400 to 320 nm, a medium wavelength ultraviolet ray of 320 to 290 nm and a short wavelength ultraviolet ray of below 290 nm. These rays are, respectively, called UV-A, UV-B and UV-C.

Ordinarily, a typical source of UV rays to which men are exposed is sunlight. Ultraviolet rays from sunlight which can reach the ground surface are UV-A and UV-B. UV-C is absorbed with the ozone layer and does rarely reach the ground surface. Of the ultraviolet rays which reach the ground surface, UV-B acts to form erythema and blisters and brings about changes in the skin such as accelerated formation of melanine, pigmentation and the like upon irradiation on the skin in amounts of light more than a certain level. In contrast, UV-A has been hitherto considered not to cause substantial changes in the skin. However, it has been recently disclosed by electron microscopic and histochemical techniques that the skin undergoes changes even through UV-A irradiation. In particular, the energy of UV-A, different from UV-B, arrives even at the inner skin and will bring about slight chronic changes in elastic fibers of blood vessel and connective tissues. These changes are considered to lead to promoted senility of the skin. It is also known that UV-A has the action of melanizing the skin (time-limit melanization) immediately after irradiation thereof and acts to increase the degenerative action of UV-B on the skin. UV-A is thus considered to be one of factors of developing and exacerbating moth patches and freckles.

As will be apparent from the above, it is important to protect the skin not only from UV-B, but also from UV-A in the sense that the skin is prevented from promoting the senility and the development and exacerbation of moth patches and freckles are prevented.

However, the studies on the action of UV-A on the skin have only a short history and only a slight number of substances capable of effectively absorbing UV-A when applied to the skin are known at present, including dibenzoylmethane derivatives and cinnamic acid derivatives (German Patent Laid-open Nos. 2728241 and 2728243, and Japanese Laid-open Patent Application Nos. 51-61641, 52-46056, 57-59840 and 57-197209).

Therefore, there is a high demand of development of protective agents which are able to absorb harmful UV-A to effectively protect the human skin therefrom. Such protective agents should satisfy the following requirements.

(1) A maximum absorbing capacity at a wavelength in the vicinity of 350 nm.

(2) A satisfactorily high molar absorptivity coefficient at the above wavelength.

(3) A small absorptivity of visible light because coloration of cosmetic compositions are not desirable, i.e. should be nearly zero ($\epsilon \approx 0$) over 400 nm.

(4) High stability against heat and light.

(5) No toxic, irritative and other harmful actions against the skin.

(6) Good compatibility with cosmetic substrates.

(7) Unlikelihood to be percutaneously absorbed upon application to the skin and removed such as by sweating, or effective continuance of the efficacy.

SUMMARY OF THE INVENTION

The present inventors have made intensive studies and found that certain types of derivatives of chalcone which is widely known as one of the components in plants satisfy the above requirements and can thus effectively protect the skin from UV-A.

Accordingly, an object of the present invention is to provide novel chalcone derivatives.

Another object of the invention to provide UV absorbers which comprise novel chalcone derivatives.

The above objects can be achieved, according to the invention, by chalcone derivatives of the following general formula (I)

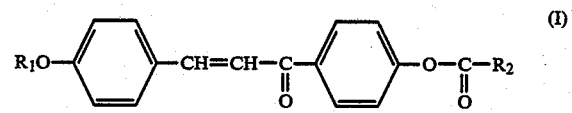

in which $R_1$ represents a hydrogen atom or a methyl group, and $R_2$ represents a linear or branched aliphatic hydrocarbon group having from 2 to 24 carbon atoms.

DETAILED DESCRIPTION OF THE INVENTION

Figure 1:
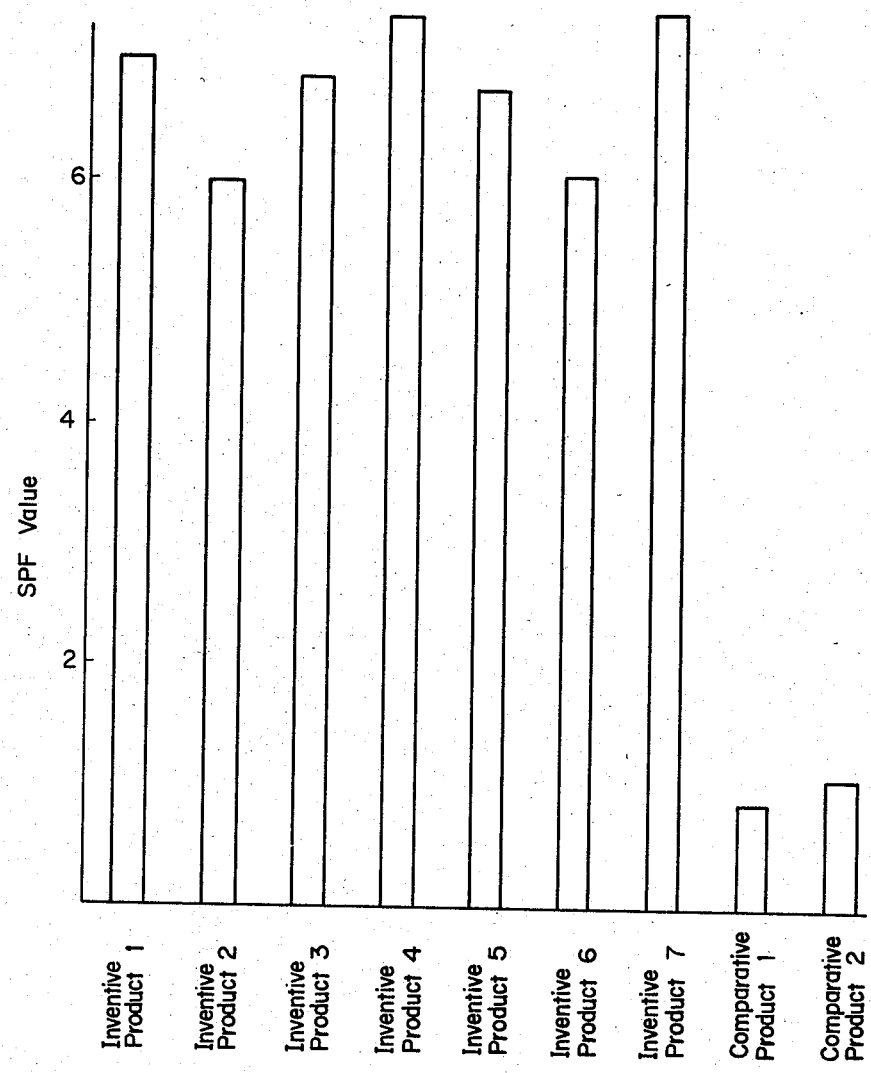
FIG. 1 is a graph showing SPF values of inventive products 1 to 7 and comparative products 1 and 2.

The novel chalcone derivatives of the invention can be prepared by techniques known per se. More particularly, as shown in the following sequence of reactions, 4-methoxybenzaldehyde and 4-hydroxyacetophenone are subjected to condensation reaction to obtain 4-alkoxy-4'-hydroxychalcone (II), followed by acylation to obtain an intended chalcone derivative (I).

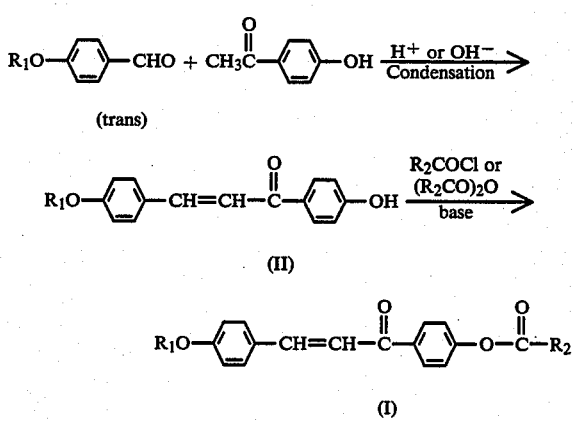

in which $R_1$ and $R_2$ have, respectively, the same meanings as defined before.

The starting hydroxychalcone (II) in which $R_1$ is a methyl group is known (T. Szell et al., Can. J. Chem., 42, 2417 (1964), Can. J. Chem., 43, 2134 (1965), D. Vorlander, Chem. Ber., 58, 118 (1925), G. Sipos et al., Chem. Abstr., 59, 5059 (1963)), and can be prepared in high yield using acid or base catalysts.

The acylation of the hydroxychalcone (II) may be carried out using ordinary acylation reactions. For instance, there is used a method in which a corresponding carboxylic acid anhydride (($R_2CO)_2O$) is reacted with the compound (II) using pyridine or a sodium salt of a corresponding carboxylic acid, or a method in which an acid chloride ($R_2COCl$) is reacted using base catalysts having no nucleophilicity.

In the compound of the general formula (I), $R_1$ is a hydrogen atom or methyl group. $R_2$ is a linear or branched aliphatic hydrocarbon group having from 2 to 24, preferably 4 to 20 carbon atoms.

The ultraviolet absorbers according to the invention are obtained by adding the compound of the general formula (I) to known substrates for cosmetics in a usual manner. The absorbers may be prepared in the form of creams, solutions, oils, sprays, sticks, emulsions, foundations and ointments.

When the compounds of the invention are mixed with ointment or cream substrates, there are obtained oily or non-oil anti-sunburn ointments or skin creams. Likewise, when the compound is mixed with solvents (or emulsifiers as the case may be), anti-sunburn oils, lotions or skin cares are obtained. Substrates or solvents suitable for the above purpose include hydrocarbons such as solid or liquid paraffins, crystal oil, ceresin, ozokerite and montan wax; plant oil, animal oils and fats, and wax such as olive oil, earth wax, carunauba wax, lanoline, sperm oil and the like; aliphatic acids and esters thereof such as stearic acid, palmitic acid, oleic acid, glycerine monostearate, glycerine distearate, glycerine monooleate, isopropyl myristate, isopropyl stearate, butyl stearate and the like; and alcohols such as ethyl alcohol, isopropyl alcohol, cetyl alcohol, stearyl alcohol, palmityl alcohol, hexyldodecyl alcohol and the like. Additionally, polyhydric alcohols serving as humectants such as glycol, glycerine or sorbitol may also be used.

The amount of compound (I) in the ultraviolet absorbers may vary depending on the type of preparation and thus is not critical. Although an effective amount of compound (I) is sufficient, the amount is generally from 0.1 to 20 wt. %, preferably 0.5 to 10 wt. %, of the composition.

Although the ultraviolet absorber of the invention may comprise compound (I) alone as an effective ingredient, it is preferred that other UV-B absorbers are used in combination for use as ordinary anti-sunburn cosmetics. Examples of the UV-B absorbers include p-methylbenzylidene-D, L-camphor or its sodium sulfonate, sodium 2-phenylbenzimidazole-5-sulfonate, sodium 3,4-dimethylphenylglyoxylate, 4-phenylbenzophenone, isooctyl 4-phenylbenzophenone-2'-carboxylate, p-methoxycinnamate, 2-phenyl-5-methylbenzoxazole, and p-dimethylaminobenzoate and the like.

Aside from the above ingredients, the ultraviolet absorbers of the invention may further comprise various additives. Suitable additives are, for example, W/O and O/W emulsifiers. These emulsifiers are commerically available. Moreover, thickeners or additives such as methyl cellulose, ethyl cellulose, carboxymethyl cellulose, polyacrylic acid, tragacanth, agar-agar and gelatine. If necessary, perfumes, preservatives, humectants, emulsion stabilizers, medical ingredients and/or physiologically permissible colorants may be added.

The present invention is described in more detail by way of experimental examples, references and examples.

EXPERIMENTAL EXAMPLE 1

Creams comprising 2% of compounds of the invention were used to determine an effect of protecting the skin from UV-A irradiation. In this test, there were used a cream of the formulation of Example 9 (inventive product 4) and creams in which there were used, instead of 4-methyoxy-4'-palmitoyloxychalcone used in the cream composition of Example 9, 4-methoxy-4'-methyl-branched isostearoyloxychalcone (inventive product 1), 4-methoxy-4'-linear stearolyloxychalcone (inventive product 2), 4-methoxy-4'-oleoyloxychalcone (inventive product 3), 4-methoxy-4'-octanoyloxychalcone (inventive product 5), 4-methoxy-4'-hexanoyloxychalcone (inventive product 6), or 4-methoxy-4'-propanoyloxychalcone (inventive product 7). The test method was carried in accordance with a method of Gschnait et al (Archives of Dermafological Research 263, 181–188 (1978)). More particularly, guinea pigs were shaved on the back thereof to expose the skin. Susceptibility to UV-A was enhanced by intracelially dosing 8-methoxypsoralen to the guinea pigs. Subsequently, the creams 1 to 7 of the invention were applied onto the exposed skins in an amount of 2 mg/cm$^2$ and 15 minutes after the application, UV-A irradiation was effected. Twenty four hours after the irradiation, the skin was observed as to whether or not erythema developed and the shortest UV-A irradiation time before erythema was produced on the skin was determined. This shortest time was compared with the shortest UV-A irradiation time before erythema developed on a non-applied skin and a sun-protecting factor (hereinafter abbreviated as SPF) was calculated according to the following equation, from which the skin-protecting effect of the respective compounds was determined. Comparative creams were a cream base alone (comparative product 1) used in Example 9 and vaseline (comparative product 2).

$$SPF = \frac{\text{Shortest UV-A irradiation time before erythema developed on the skin on which the cream of the invention was applied}}{\text{Shortest UV-A irradiation time before erythema developed on the non-applied skin}}$$

The results of this test revealed that the cream base alone and vaseline could not protect the skin from the ultraviolet light, but the creams comprising 2% of the compounds of the invention exhibited SPF values of about 6 to 8, effectively protecting the skin from the UV-A light.

REFERENCE 1

Synthesis of 4-methoxy-4'-hydroxychalcone:

Into an ethanol solution (5 liters) comprising 500 g (3.67 moles) of anisaldehyde and 500 g (3.67 moles) of 4-hydroxyacetophenone was dropped an aqueous solution (600 ml) of 250 g of sodium hydroxide in about 80 minutes in a stream of nitrogen. Thereafter, the mixture was heated to 50° C. and agitated for 24 hours. The reaction mixture was cooled down to room temperature, to which were added 2 liters of 12% hydrochloric acid and then 4 liters of water, whereupon crystals settled. The crystals were collected by filtration and quickly washed with ethanol, followed by drying under reduced pressure to obtain 750 g of the intended compound (2.95 moles, yield 80%). The compound was recrystallized from ethanol to obtain light yellow prismatic purified crystals. The melting point and various spectral data of the compound coincided with those of a reference compound.

Melting point 189.5° C. (188° to 190° C. for reference compound)

EXAMPLE 1

Synthesis of 4-methoxy-4'-methyl-branched isostearoyloxychalcone:

10.17 g (0.04 mole) of 4-methyoxy-4'-hydroxychalcone obtained in Reference 1 and 6.33 g (0.080 mole) of pyridine were dissolved in 100 ml of methylene chloride which had been preliminarily dried with calcium chloride, into which was dropped a dried methylene chloride (20 ml) solution of methyl-branched isostearoyl chloride in 10 minutes under ice-cooling and agitating conditions. The mixture was allowed to stand at room temperature overnight and refluxed for 20 minutes in order to complete the reaction. The reaction mixture was poured into ice-cold water, to which was added concentrated hydrochloric acid to render the mixture acidic (pH=1), followed by extraction with chloroform. The chloroform phase was washed with a saturated sodium bicarbonate aqueous solution, followed by drying with anhydrous sodium sulfate and removing the solvent by distillation under reduced pressure to obtain the intended compound substantially quantitatively. The compound had such a melting point and spectral data as indicated in Tables 1 and 2.

EXAMPLES 2 to 7

The general procedure of Example 1 was repeated using, instead of the methyl-branched isostearoyl chloride, propionyl chloride, hexanoyl chloride, octanoyl chloride, palmitoyl chloride, stearoyl chloride and oleoyl chloride, thereby obtaining intended compounds. The melting points and various spectral data of these compounds are shown in Tables 1 and 2.

TABLE 1

| Example | Formula (I) $R_1$ | $R_2CO$ | Melting Point (°C.) | Yield (%) | Elemental Analysis (Calcd) C (%) | H (%) | UV (CHCl$_3$) $\lambda$max (nm) | $\epsilon(\log_e)$ | IR(cm$^{-1}$, KBr) $\gamma_{c=o}$ |
|---|---|---|---|---|---|---|---|---|---|
| 1 | CH$_3$ | C$_{17}$H$_{35}$CO (methyl-branched isostearoyloxy) | 40–50 | 100 | | | 341 | 23100 (4.36) | 1620, 1650 1740 |
| 2 | " | C$_2$H$_5$CO | 87.0–87.5 | 80 | 73.41 (73.53) | 6.14 (5.85) | 341 | 21700 (4.34) | 1625, 1660, 1740 |
| 3 | " | C$_5$H$_{11}$CO | 69.2–69.5 | 82 | 74.92 (74.98) | 6.86 (6.86) | 341 | 22300 (4.35) | 1620, 1650 1740 |
| 4 | " | C$_7$H$_{15}$CO | 76.3–76.7 | 95 | 75.80 (75.76) | 7.29 (7.42) | 341 | 22600 (4.36) | 1620, 1650 1735 |
| 5 | " | C$_{15}$H$_{31}$CO | 93.0–94 | 95 | 77.93 (78.01) | 8.92 (9.00) | 341 | 25600 (4.41) | 1625, 1650 1740 |
| 6 | " | C$_{17}$H$_{35}$CO | 90.3–91.4 | 89 | 78.38 (78.42) | 9.31 (9.29) | 341 | 22200 (4.35) | 1625, 1650 1740 |
| 7 | " | C$_{17}$H$_{33}$CO (oleoyloxy) | 55.4–56.4 | 87 | 78.98 (78.72) | 8.66 (8.94) | 341 | 22900 (4.36) | 1625, 1655, 1740 |

TABLE 2

| Example | Formula (I) $R_1$ | $R_2CO$ | —NMR Data (CDCl$_3$, δ, TMS Internal Standard) OCH$_3{}^a$ | Ar—H$^b$ | C=C—H$^c$ | —COR$_2$ |
|---|---|---|---|---|---|---|
| 1 | CH$_3$ | C$_{17}$H$_{35}$CO (methyl-branched isostearoyloxy | 3.78 | 6.87(2H, d) 7.17(2H, d) 7.55(2H, d) 8.03(2H, d) | 7.30(1H, d) 7.80(1H, d) | 0.6–2.0(33H, m, —C$_{15}$$\underline{H}$$_{33}$) 2.56(2H, t, J = 7.0 Hz, —CO—C$\underline{H}$$_2$—) |
| 2 | " | C$_2$H$_5$CO | 3.80 | 6.86(2H, d) 7.17(2H, d) 7.54(2H, d) 8.02(2H, d) | 7.30(1H, d) 7.80(1H, d) | 1.24(3H, t, J = 6.0 Hz, —C$\underline{H}$$_3$) 2.58(2H, q, J = 7.5 Hz, —CO—C$\underline{H}$$_2$—) |
| 3 | " | C$_5$H$_{11}$CO | 3.79 | 6.87(2H, d) 7.17(2H, d) 7.55(2H, d) 8.03(2H, d) | 7.30(1H, d) 7.80(1H, d) | 0.89(3H, t, J = 6.0 Hz, —C$\underline{H}$$_3$) 0.7–2.1(6H, m, —(C$\underline{H}$$_2$)$_3$—) 2.53(2H, t, J = 7.0 Hz, —CO—C$\underline{H}$$_2$—) |
| 4 | " | C$_7$H$_{15}$CO | 3.80 | 6.87(2H, d) 7.17(2H, d) 7.55(2H, d) 8.03(2H, d) | 7.30(1H, d) 7.80(1H, d) | 0.88(3H, t, J = 6.0 Hz, —C$\underline{H}$$_3$) 0.7–2.1(10H, m, —(C$\underline{H}$$_2$)$_5$—) 2.55(2H, t, J = 7.0 Hz, —CO—C$\underline{H}$$_2$—) |
| 5 | " | C$_{15}$H$_{31}$CO | 3.81 | 6.87(2H, d) 7.17(2H, d) 7.55(2H, d) 8.03(2H, d) | 7.30(1H, d) 7.80(1H, d) | 0.87(3H, t, J = 6.0 Hz, —C$\underline{H}$$_3$) 0.7–2.1(26H, m, —(C$\underline{H}$$_2$)$_{13}$—) 2.55(2H, t, J = 7.0 Hz, —CO—C$\underline{H}$$_2$—) |
| 6 | " | C$_{17}$H$_{35}$CO | 3.80 | 6.87(2H, d) 7.17(2H, d) 7.55(2H, d) 8.03(2H, d) | 7.30(1H, d) 7.80(1H, d) | 0.86(3H, t, J = 6.0 Hz, —C$\underline{H}$$_3$) 0.6–2.1(30H, m, —(C$\underline{H}$$_2$)$_{15}$—) 2.56(2H, t, J = 7.0 Hz, —CO—C$\underline{H}$$_2$—) |
| 7 | " | C$_{17}$H$_{33}$CO (oleoyloxy) | 3.83 | 6.87(2H, d) 7.17(2H, d) 7.55(2H, d) | 7.30(1H, d) 7.80(1H, d) | 0.89(3H, t, J = 6.0 Hz, —C$\underline{H}$$_3$) 0.7–2.5(28H, m, —C$_{15}$$\underline{H}$$_{28}$—) 2.56(2H, t, J = 7.0 Hz, —CO—C$\underline{H}$$_2$—) |

TABLE 2-continued

| | Formula (I) | | —NMR Data (CDCl$_3$, δ, TMS Internal Standard) | | | |
|---|---|---|---|---|---|---|
| Example | R$_1$ | R$_2$CO | OCH$_3$[a] | Ar—H[b] | C=C—H[c] | —COR$_2$ |
| | | | | 8.03(2H, d) | | |

[a] 3H, s.
[b] J = 8.5 Hz.
[c] J = 16 Hz.

EXAMPLE 8

O/W Type Cream:

A composition of the following formulation was prepared in a usual manner to obtain an O/W type cream.

| [Formulation] | |
|---|---|
| 4-Methoxy-4'-methyl-branched isostearoyloxychalcone | 2.0 wt % |
| Stearic acid | 1.0 |
| Oleophilic monostearic glyceride | 2.0 |
| Polyoxyethylene sorbitan monostearate | 1.0 |
| Cetyl alcohol | 1.0 |
| Stearyl alcohol | 1.0 |
| Squalane | 10.0 |
| Liquid paraffin | 20.0 |
| Vaseline | 5.0 |
| Butylparaben | 0.1 |
| Methylparaben | 0.1 |
| Triethanolamine | 1.0 |
| Glycerine | 10.0 |
| Perfume | suitable amount |
| Water | balance |
| | 100.0 |

EXAMPLE 9

W/O Type Cream:

A composition of the following formulation was used to prepare a W/O type cream.

| [Formulation] | |
|---|---|
| 4-Methoxy-4'-palmitoyloxychalcone | 2.0 wt % |
| Sorbitan sesquioleate | 4.0 |
| Aluminium stearate | 0.5 |
| Cetyl alcohol | 4.0 |
| Liquid paraffin | 16.0 |
| Squalane | 10.0 |
| Isopropyl myristate | 5.0 |
| Sodium benzoate | 0.3 |
| Glycerine | 10.0 |
| Perfume | suitable amount |
| Water | balance |
| | 100.0 |

EXAMPLE 10

O/W Type Emulsion:

A composition of the following formulation was used to prepare an O/W type emulsion.

| [Formulation] | |
|---|---|
| 4-Methoxy-4'-octanoyloxychalcone | 3.0 wt % |
| Stearic acid | 2.0 |
| Sorbitan monostearate | 1.5 |
| Polyoxyethylenesorbitan monostearate | 1.0 |
| Cetyl alcohol | 0.4 |
| Stearyl alcohol | 0.3 |
| Isopropyl myristate | 7.0 |
| Squalane | 5.0 |
| Liquid paraffin | 5.0 |
| Solid paraffin | 2.0 |

-continued

| [Formulation] | |
|---|---|
| Ethylparaben | 0.1 |
| Methylparaben | 0.1 |
| Carbopol | 0.2 |
| Caustic potash | 0.4 |
| Perfume | suitable amount |
| Water | balance |
| | 100.0 |

EXAMPLE 11

Lotion:

A composition of the following formulation was used to prepare a lotion.

| [Formulation] | |
|---|---|
| 4-Methoxy-4'-hexanoyloxychalcone (product of the invention) | 2.0 wt % |
| Polyoxyethylene (23) lauryl ether | 4.0 |
| Ethanol | 10.0 |
| Glycerine | 3.0 |
| Dipropylene glycol | 7.0 |
| Lactic acid | 0.05 |
| Sodium lactate | 0.12 |
| Methylparaben | 0.1 |
| Perfume | suitable amount |
| Colorant | small amount |
| Water | balance |
| | 100.0 |

What is claimed is:

1. A chalcone compound of the formula (I)

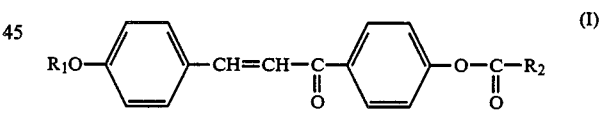

in which R$_1$ represents a hydrogen atom or a methyl group, and R$_2$ represents a linear or branched aliphatic hydrocarbon group having from 7 to 24 carbon atoms.

2. An ultraviolet absorbing composition comprising an effective amount of a chalcone compound of the formula (I)

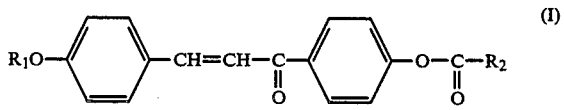

in which R$_1$ represents a hydrogen atom or a methyl group, and R$_2$ represents a linear or branched aliphatic hydrocarbon group having from 7 to 24 carbon atoms.

3. An ultraviolet absorbing composition absorbing both UV-A and UV-B radiation which comprises an effective amount of a chalcone compound of the formula (I)

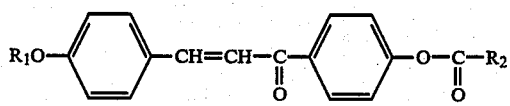

which absorbs UV-A radiation, in which $R_1$ represents a hydrogen atom or a methyl group, and $R_2$ represents a linear or branched aliphatic hydrocarbon group having from 2 to 24 carbon atoms, and an effective amount of a UV-B radiation absorbing compound.

4. The ultraviolet absorbing composition of claim 3, wherein said UV-B radiation absorbing compound is selected from the group consisting of p-methylbenzylidene-D, L-camphor or its sodium sulfonate, sodium-2-phenylbenzimidazole-5-sulfonate, sodium 3,4-dimethylphenylglyoxylate, 4-phenylbenzophenone, isooctyl 4-phenylbenzophenone-2'-carboxylate, p-methoxycinnamate, 2-phenyl-5-methylbenzoxazole, and p-dimethylaminobenzoate.

5. The ultraviolet absorbing composition of claim 3, wherein said UV-A radiation absorbing compound of formula (I) is present in the amount of about 0.1–20 wt. % based on the total weight of the composition.

6. The ultraviolet absorbing composition of claim 3, wherein $R_2$ of said UV-A radiation absorbing compound of formula (I) has 7 to 24 carbon atoms.

* * * * *